(12) United States Patent
Penenberg

(10) Patent No.: US 7,582,090 B2
(45) Date of Patent: Sep. 1, 2009

(54) BONE PRESERVING TOTAL HIP ARTHROPLASTY USING AUTOGRAFT

(75) Inventor: Brad L. Penenberg, Los Angeles, CA (US)

(73) Assignee: Wright Medical Technology, Inc., Arlington, TN (US)

( * ) Notice: Subject to any disclaimer, the term of this patent is extended or adjusted under 35 U.S.C. 154(b) by 900 days.

(21) Appl. No.: 10/793,355

(22) Filed: Mar. 4, 2004

(65) Prior Publication Data

US 2005/0203524 A1  Sep. 15, 2005

(51) Int. Cl.
*A61F 5/00* (2006.01)

(52) U.S. Cl. .............................. 606/79; 606/89; 606/99; 606/86 R

(58) Field of Classification Search ................... 606/86, 606/79, 89, 62, 99, 105
See application file for complete search history.

(56) References Cited

U.S. PATENT DOCUMENTS

| | | | | |
|---|---|---|---|---|
| 3,815,599 | A * | 6/1974 | Deyerle | 606/85 |
| 4,921,493 | A * | 5/1990 | Webb et al. | 606/85 |
| 4,957,510 | A | 9/1990 | Cremascoli | |
| 5,006,121 | A * | 4/1991 | Hafeli | 606/85 |
| 5,089,003 | A * | 2/1992 | Fallin et al. | 606/85 |
| 5,470,336 | A * | 11/1995 | Ling et al. | 606/105 |
| 5,507,830 | A * | 4/1996 | DeMane et al. | 623/22.42 |
| 5,683,395 | A * | 11/1997 | Mikhail | 606/86 |
| 5,800,437 | A * | 9/1998 | Gustilo et al. | 606/86 |
| 5,810,830 | A * | 9/1998 | Noble et al. | 606/85 |
| 5,899,907 | A * | 5/1999 | Johnson | 606/73 |
| 5,910,172 | A | 6/1999 | Penenberg | |
| 6,013,080 | A * | 1/2000 | Khalili | 606/86 |
| 6,015,408 | A * | 1/2000 | Pichon et al. | 606/53 |
| 6,126,659 | A * | 10/2000 | Wack | 606/60 |
| 6,193,759 | B1 * | 2/2001 | Ro et al. | 623/23.28 |
| 6,224,605 | B1 * | 5/2001 | Anderson et al. | 606/85 |
| 6,270,502 | B1 | 8/2001 | Stulberg | |
| 6,309,395 | B1 | 10/2001 | Smith | |
| 6,589,285 | B2 | 7/2003 | Penenberg | |
| 6,656,188 | B2 | 12/2003 | Naybour | |
| 2004/0015239 | A1 | 1/2004 | LeBeguec | |
| 2004/0024471 | A1 | 2/2004 | Ferree | |

* cited by examiner

*Primary Examiner*—Eduardo C Robert
*Assistant Examiner*—Mary Hoffman

(57) ABSTRACT

Methods and instruments for use of a patient's native and existing cancellous bone as a packing material for the intramedullary canal in total hip arthroplasty and subsequent revision hip surgery. A series of tamps of progressively larger size are used to pack the native cancellous bone, the tamps having a shape substantially similar to that of the hip prosthesis. The methods and instruments are bone conserving. If the patient later needs a revision surgery, the doctor has more bone to work with and there is less risk of complications.

5 Claims, 10 Drawing Sheets

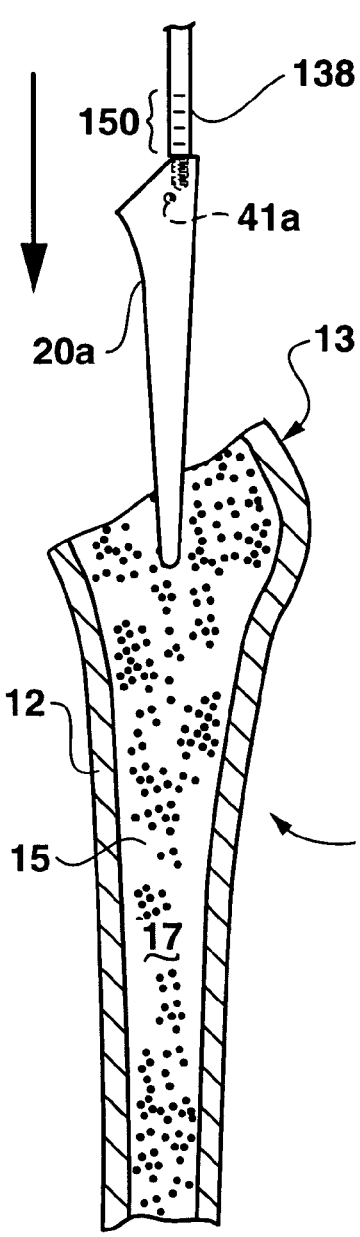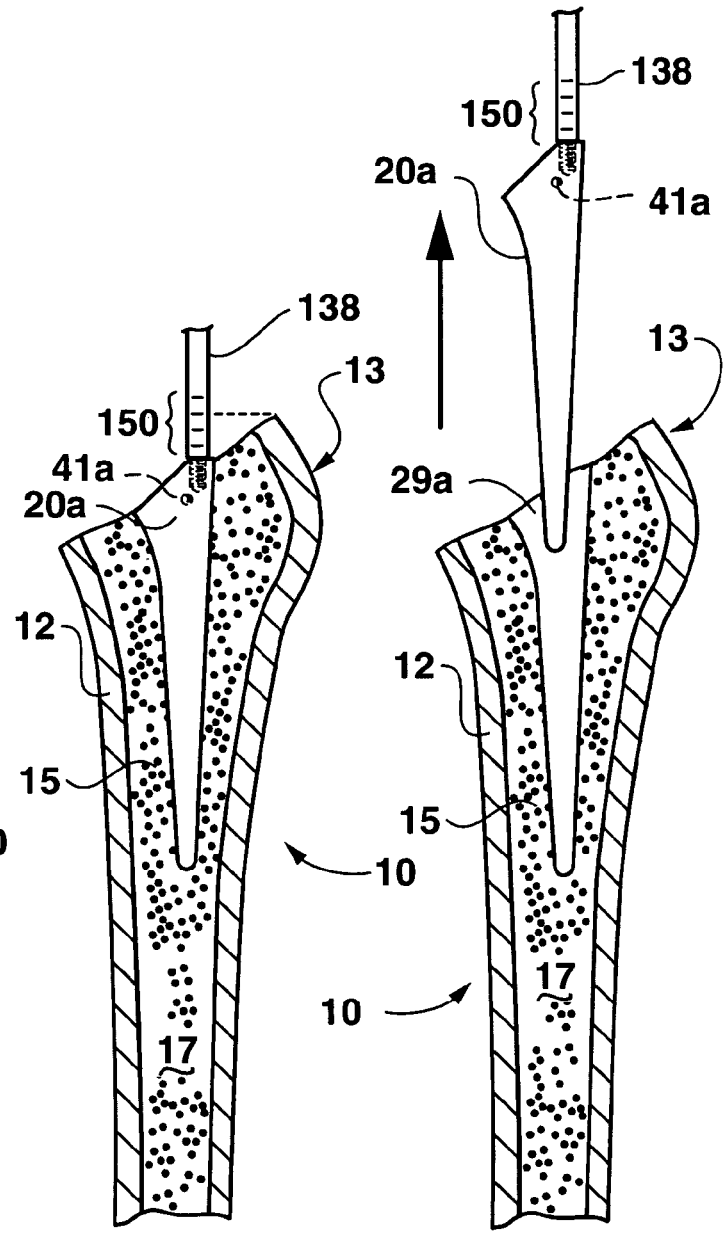
FIG. 5A  FIG. 5B  FIG. 5C

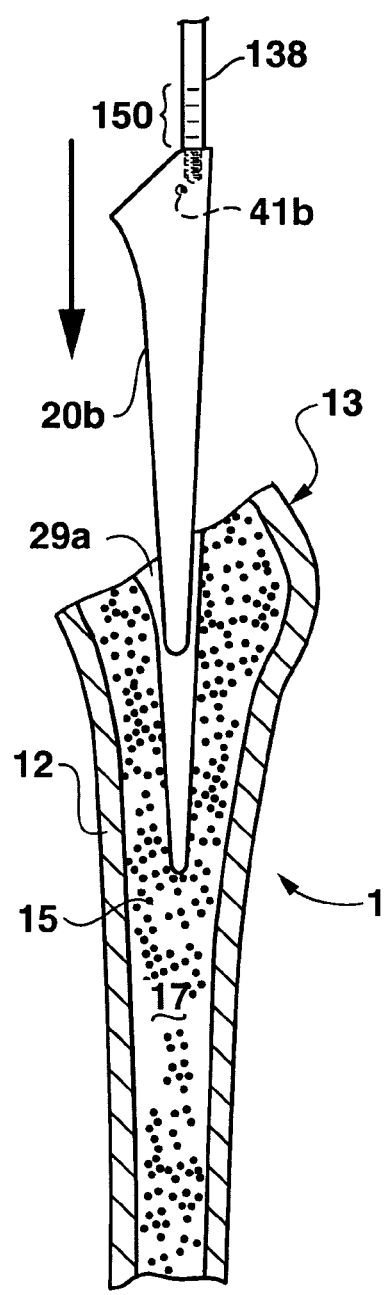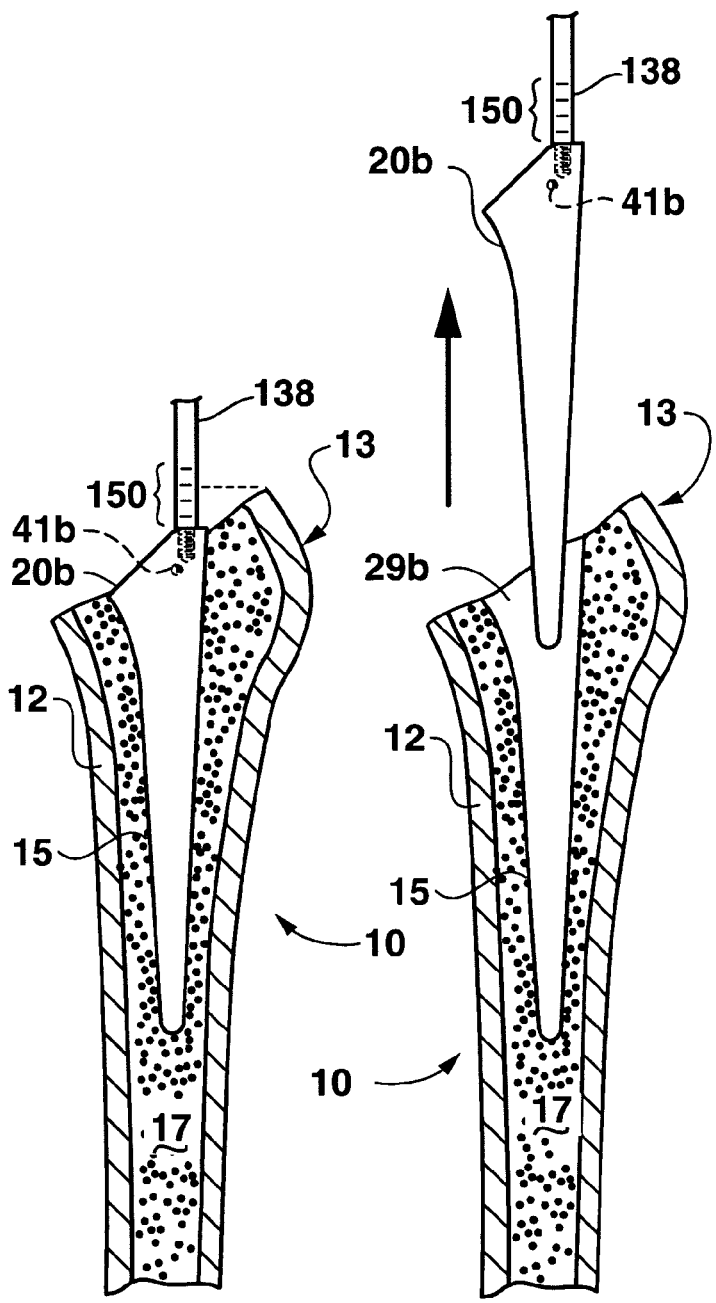
FIG. 6A FIG. 6B FIG. 6C

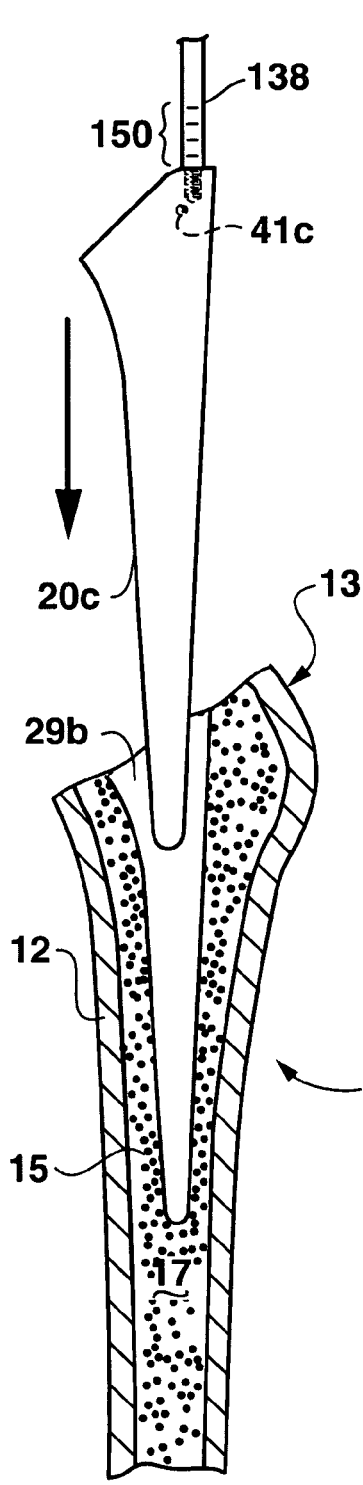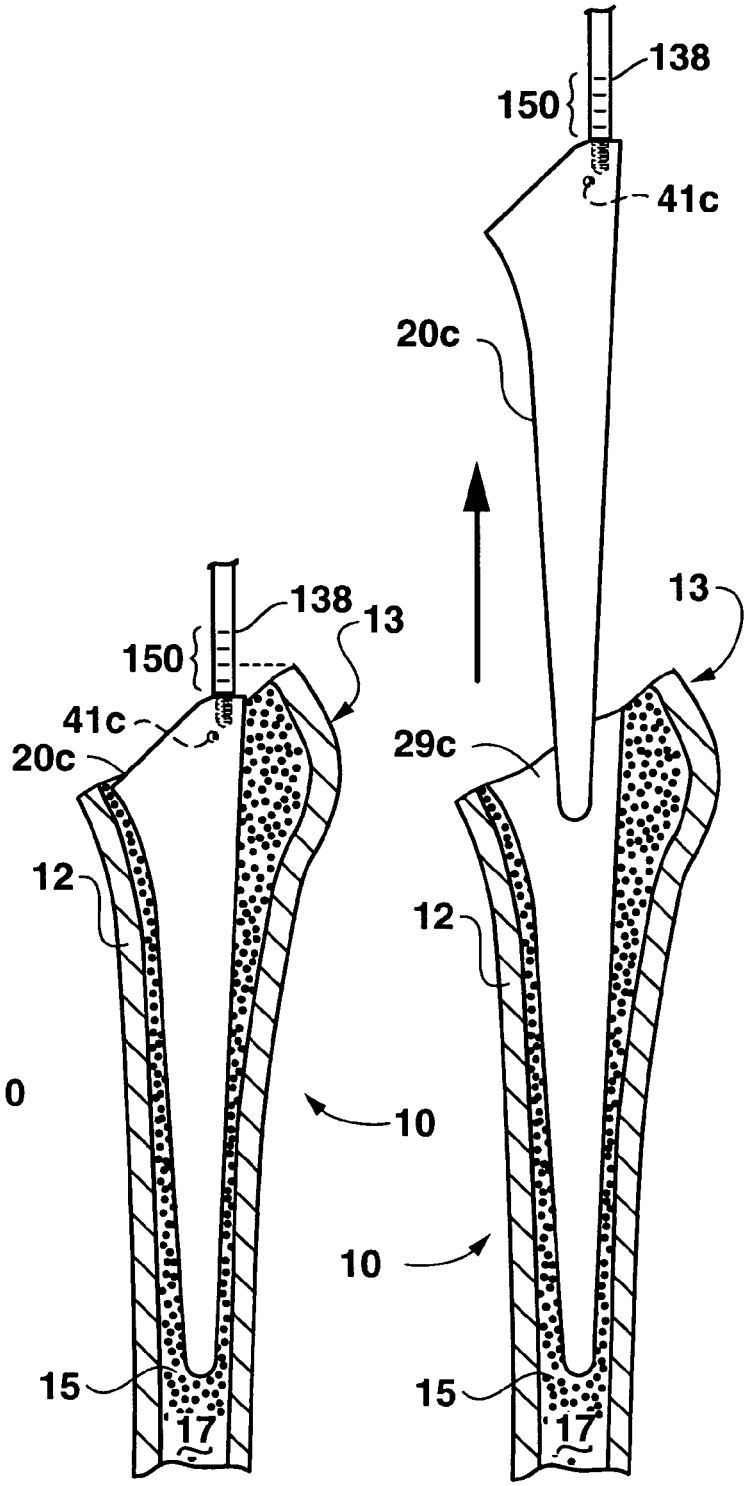
FIG. 7A  FIG. 7B  FIG. 7C

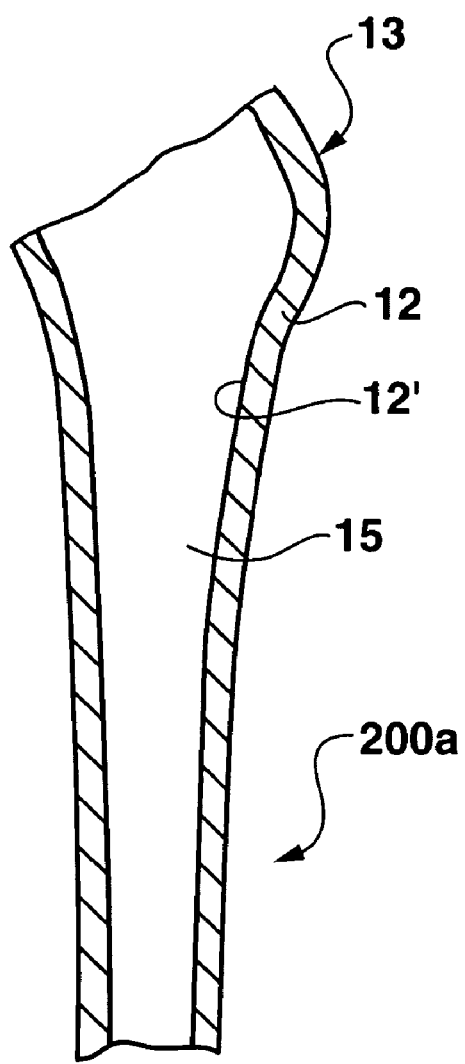 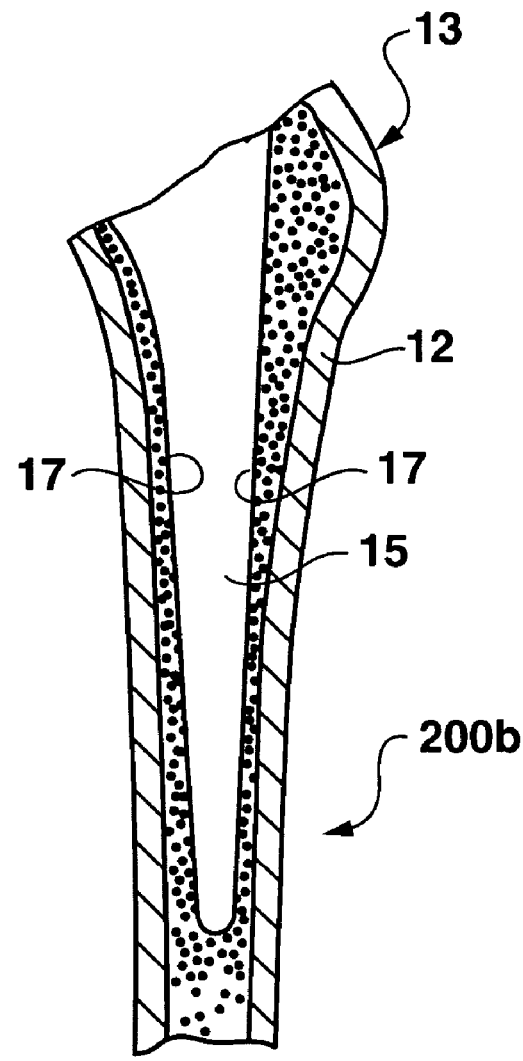
FIG. 10A  FIG. 10B

BONE PRESERVING TOTAL HIP ARTHROPLASTY USING AUTOGRAFT

FIELD OF THE INVENTION

This invention is generally directed to total hip arthroplasty (THA). The invention is more specifically directed to primary THA using autograft in the form of the patient's native and existing cancellous bone as a packing material for the intramedullary canal.

BACKGROUND OF THE INVENTION

The use of tamps to pack a graft material into the intramedullary canal of a femur is known. However, such processes have been typically used in revision applications where there is no longer any cancellous bone within the intramedullary canal of the femur. It has been suggested to tamp a graft material within the intramedullary canal of a femur during primary applications, but only as a modification of a method intended primarily for revision applications (U.S. Pat. Nos. 5,192,283 and 6,270,502) or as an instrument for providing a graft material into a fully broached intramedullary canal from an external source of graft material (U.S. Pat. No. 6,309,395). All patents and patent application referred to in this patent application are incorporated by reference herein in their entirety.

Practical experience has shown that prior art methods do not meet the needs of, especially, the modern primary THA patient, who may now be in their early 30's and most likely face one or more revision hip surgeries at some point in their lives.

Accordingly, there is room for improvement within the art.

OBJECTS OF THE INVENTION

It is an object of the invention to provide an improved method of performing a total hip arthroplasty.

It is a further object of the invention to provide an improved method of performing a primary total hip arthroplasty.

It is a further object of the invention to provide an improved method of performing a primary total hip arthroplasty that better prepares the patient for a potential later revision hip surgery.

These and other objects of the invention are achieved by a method for performing hip surgery, comprising the steps of: accessing the intramedullary canal of a femur, the intramedullary canal containing cancellous bone; providing a first tamp, the tamp having a shape substantially similar to that of the prosthesis to be implanted; impacting a first tamp into the cancellous bone of the intramedullary canal; removing the first tamp, thereby forming a first cavity having a shape substantially similar to that of the prosthesis to be implanted in the cancellous bone of the intramedullary canal.

These and other objects of the invention are achieved by a tamp for use in performing hip surgery, comprising: a body, the body shaped substantially the same as the prosthesis to be implanted; the body further comprising a bore for receipt of a trial neck and head.

These and other objects of the invention are achieved by a tamp for use in performing hip surgery, comprising: a body, the body shaped substantially the same as the prosthesis to be implanted; the body further comprising a bore for receipt of an adjustment rod.

These and other objects of the invention are achieved by a tamp for use in performing hip surgery, comprising: a body, the body shaped substantially the same as the prosthesis to be implanted; the body having a smooth surface.

These and other objects of the invention are achieved by a method of performing revision hip arthroplasty, including the steps of: removing a primary implant from the intramedullary canal of the hip; implanting the revision implant in a cavity of the patient's native cancellous bone.

These and other objects of the invention are achieved by a method of performing hip surgery, including the step of using the patient's native cancellous bone to form a cavity for receipt of the femoral prosthesis.

BRIEF DESCRIPTION OF THE DRAWINGS

FIGS. 5A, 5B, and 5C depict a first series of steps of the invention as carried out with the exemplary tamp of FIG. 4A.

FIGS. 6A, 6B, and 6C depict a potential second series of steps of the invention as carried out with the exemplary tamp of FIG. 4B.

FIGS. 7A, 7B, and 7C depict a potential third series of steps of the invention as carried out with the exemplary tamp of FIG. 4C.

FIGS. 10A and 10B compare pre-revision femurs that have undergone conventional and the inventive preparations, respectively.

DETAILED DESCRIPTION OF THE INVENTION

Figure 1:
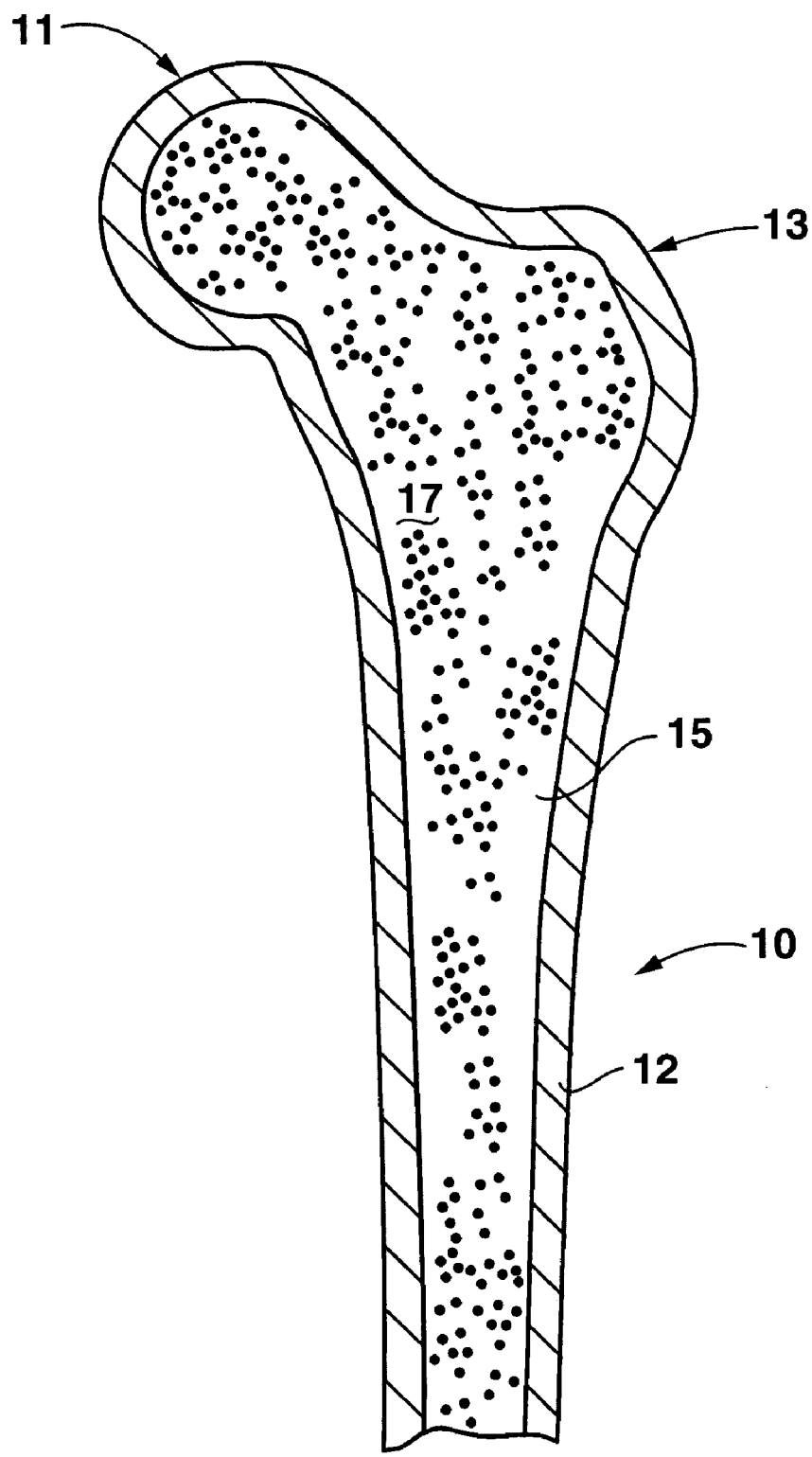
FIG. 1 is a cross-section of an intact femur.
Figure 2:
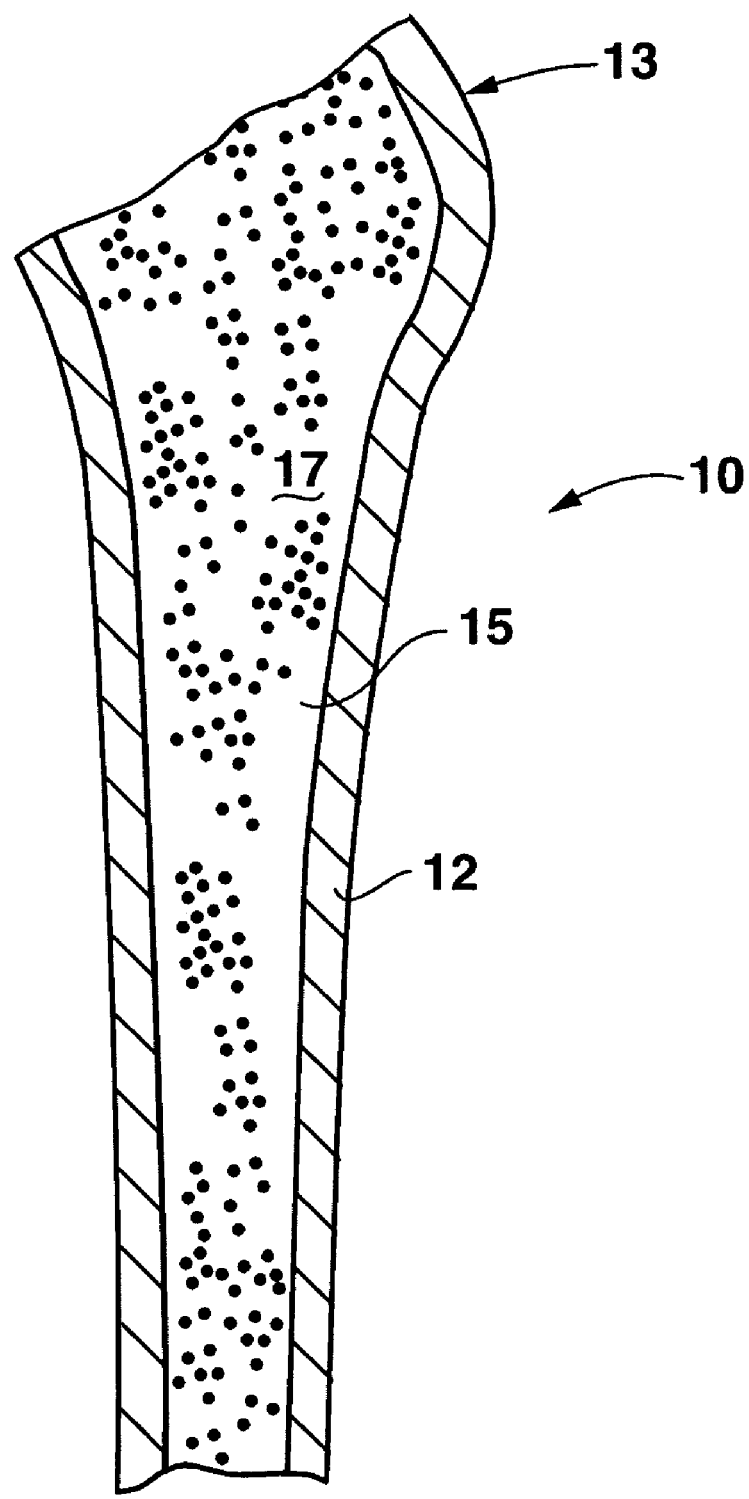
FIG. 2 is a cross-section of a femur its intramedullary canal and cancellous bone have been accessed.

With respect to the above-referenced Figures, an exemplary method of performing a THA that meets and achieves the various objects of the invention set forth above will now be described.

As mentioned above, the use of tamps to pack a graft material into the intramedullary canal of a femur is known. However, such processes have been typically used in revision applications where there is no longer any cancellous bone within the intramedullary canal of the femur.

I have discovered various problems with these prior art methods.

I. Prior Art Methods do not Resolve the Issue of How to Handle Primary Hip Patients.

While ways of improving revision surgeries are welcome, it would be much more beneficial if the primary surgery can be performed in such a way that if and when the revision surgery needs to be performed, the revision surgery itself will be less risky to the patient with more available tissue and bone for the surgeon to work with.

For example, traditional methods of femoral bone preparation for placement of cementless primary hip components are directed toward achieving what has been referred to as "fit and fill". This means that primary fixation of the femoral prosthesis is achieved by direct contact of the metal prosthesis with the inner wall of the cortical bony tube known as the intramedullary canal. In order to achieve this, healthy cancellous bone is completely removed from the intramedullary canal. There are at least three very significant disadvantages to this conventional approach. First, in the event that revision surgery is required, there is greater risk of damage to the remaining femoral cortical bone because of the absence of any space between the metal instruments or implant and the hard cortical bone. Any attempt to insert a removal type instrument can easily result in fracture of the cortical bone. Second, there is less bony support available should revision become necessary because all that remains is cortical bone. This potentially compromises the result of any revision operation. Third, the femoral bone remodels over time in the presence of an implant. In the presence of canal filling stems, significant proximal femoral bone loss (stress shielding) is known to occur. This too, increases the risk of cortical bone fracture if revision surgery is required. In addition, with the loss of bone strength and support the bending moment on the femoral prosthesis increases and fracture of the prosthesis is also known to occur. In contrast, when less bulky, non-canal filling stems are used it has been shown that the upper femoral bone can maintain its strength. This is particularly important as we have implants and bearing surfaces available with the possibility of lasting 30 years or more. This is permitting the use of THA in younger patients. The adverse consequences of these "fit and fill", canal filling stems take on greater significance.

II. Prior Art Methods Deal with Non-Autograft Materials.

As is known in the art, autograft, or bone material taken or harvested directly from the patient in question (i.e., bone native to the patient), is the gold standard of bone graft materials. This is because there is no fear of tissue rejection. However, most previously mentioned graft packing methods use non-autograft materials. While U.S. Pat. No. 6,270,502 discusses the potential use of autograft, it should be noted that it implies the use of processed autograft (see col. 8, lines 34-35). As will be described below, the method of the invention requires no such processing and the autograft is never removed from the patient's body, thereby protecting and preserving its quality as well as quantity.

FIG. 1 is a cross-section of an intact femur 10. Femur 10 includes a femoral head 11 and greater trochanter 13. The femur 10 comprises an intramedullary canal 15 surrounded by cortical bone 12. Within the intramedullary canal 15 is soft spongy bone known as cancellous bone 17.

The intramedullary canal 15 is provided in successive horizontal planes with horizontal or lateral dimensions which increase at progressive distances upwardly from the bottom of the intramedullary canal 15. Furthermore, the shape of the intramedullary canal 15 in these successive planes may change from a circle to a shape approaching a rectangle. This may be seen from a comparison of the sections in FIGS. 7, 8, 9 and 10 of U.S. Pat. No. 5,910,172.

Figures 4A, 4B, 4C:
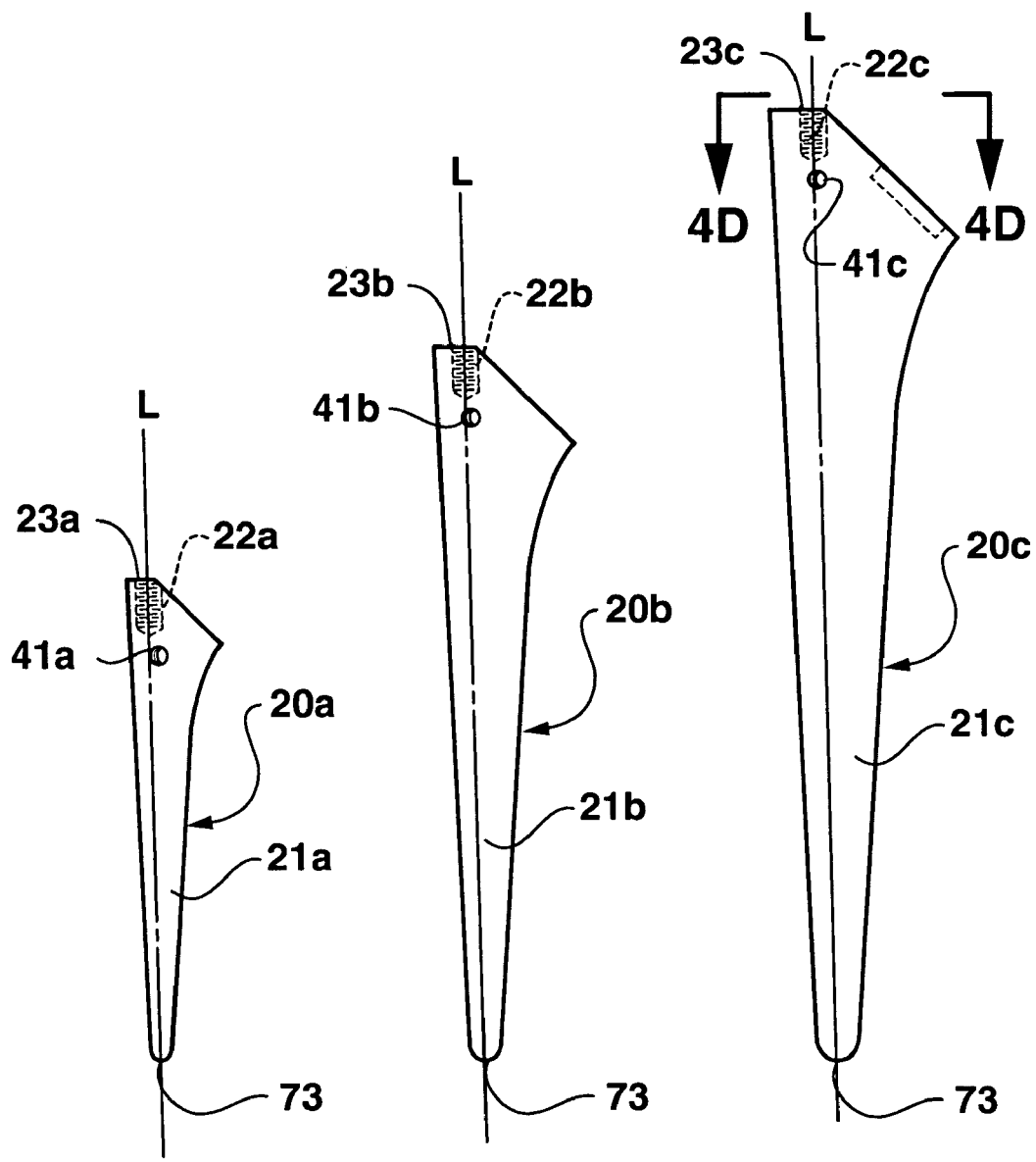
FIGS. 4A, 4B, and 4C are elevation views of exemplary tamps for use with the invention.

According to the invention, a plurality of exemplary tamps generally indicated at 20*a* (FIG. 4A), 20*b* (FIG. 4B), and 20*c* (FIG. 4C) are constructed to be disposed in sequence in the intramedullary canal 15 to pack the cancellous bone 17 in the intramedullary canal 15. Each of the tamps 20*a*, 20*b*, and 20*c* may be made from any suitable material such as stainless steel or plastic and should have a smooth surface. Smooth surfaced tamps only allow cancellous bone 17 to be pushed in a radial direction. Broach-like devices, having irregular surfaces, such as mentioned in U.S. Pat. No. 5,899,907, are known to only push cancellous bone 17 distally, which would not work with the inventive method.

Although three tamps 20*a*, 20*b*, 20*c* are illustratively provided in this exemplary embodiment of the invention, it will be appreciated that any number of tamps (more than one) may be provided without departing from the scope of the invention. These tamps may comprise what are known as "trials" or comprise additional components in the instrument kit for carrying out the THA. As generally known in the art, a trial is a component that is used to represent a prosthesis during a surgery to verify location, such as varus, valgus, anteversion (rotation), and insertion (proximal-distal location in femur), without having to risk damage to the actual prosthesis.

Each of the tamps 20*a*, 20*b*, 20*c* may be constructed in a similar manner. For example, the tamps 20*a*, 20*b*, 20*c* are respectively provided with bodies 21*a*, 21*b*, 21*c* and 21*d* having contours that are similar to the shape of a typical hip stem. This is different from prior art devices where different instruments that are not shaped at least substantially like the prosthesis to be implanted are used to prepare the intramedullary canal for different portions of the hip stem, such as mentioned in U.S. Pat. No. 5,899,907. Tamps 20*a*, 20*b*, and 20*c* are also respectively provided with threaded bores 22*a*, 22*b*, 22*c* on their respective proximal faces 23*a*, 23*b*, 23*c* for connecting the tamps to a tamp handle 138. However, any connection method may be used. Threaded bores 22*a*, 22*b*, 22*c* are in-line with the longitudinal axes L of their respective tamps 20*a*, 20*b*, 20*c*. This in-line positioning, coupled with the fact that the diameter of the impacting instrument will typically be substantially less than (at least half) the width of tamp 20 will make the method according to the invention very friendly to minimally invasive techniques (by providing clearance from anatomical features such as the remainder of the greater trochanter 13) and allow for precise positioning of tamps 20 with respect to the longitudinal axes of the intramedullary canal 15 of the femur 10. Tamp handle 138 may have calibrated hash marks 150 thereon for assisting the doctor in making sure tamps 20*a*, 20*b*, 20*c* are inserted to the proper depth, as will be described below.

The dimensions of each of the bodies 21*a*, 21*b*, 21*c* are different from the dimensions of the other ones of the bodies, become sequentially larger, and the body of the final tamp in the series will preferably have a size and shape that precisely matches that of the prosthesis to be implanted in the prepared intramedullary canal 15 of femur 10. However, it is possible for small tolerances to be allowed so long as leg length will not be affected and the final prosthesis will be firmly supported within the final cavity created by the final tamp.

Figure 4D:
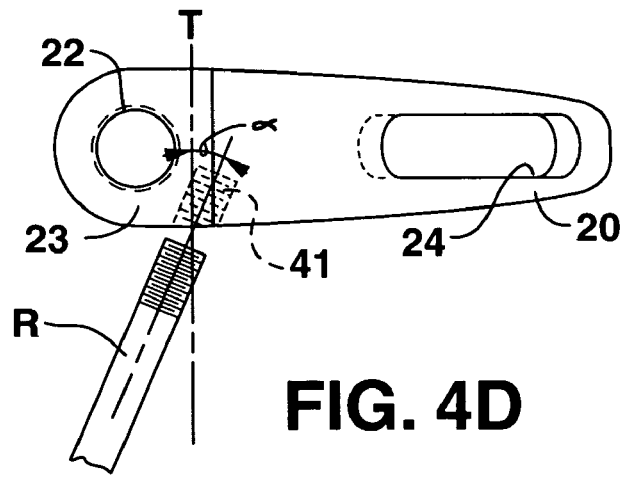
FIG. 4D is a top view of an exemplary tamp for use with invention.

As shown in FIG. 4D, each tamp 20 may also have a bore 41 in a side thereof for use in assuring its proper positioning within the intramedullary canal of the femur. To this end, each bore 41 is angled at an angle α, which is approximately 20° with respect to the transverse axis T of the tamp 20. Typically, bore 41 will be threaded for receipt of a threaded adjustment rod R. However, keyed bores and rods may also be used. The use of bore 41 and and associated rod R will be described below.

Finally, tamps 20 may have a bore 24 in its proximal body for receipt of a trial neck and head, as will be described.

Having described the structure of tamps 20*a*, 20*b*, 20*c*, their use with the method according to the invention will now be described.

As opposed to prior art tamping and graft packing methods, typically used in revision methods, with the method according to the invention, an intact femur 10, such as shown in FIG. 1, is operated on to provide access to the intramedullary canal 15 and its cancellous bone 17. This may include, but not necessarily require, resection of the femoral head 11 and a portion of the greater trochanter 13. As used herein, "intact femur", does not necessarily mean a femur that is not diseased. Rather, an intact femur means a femur that has not been subject to a previous hip surgery and has most of its original structure.

Figure 3:
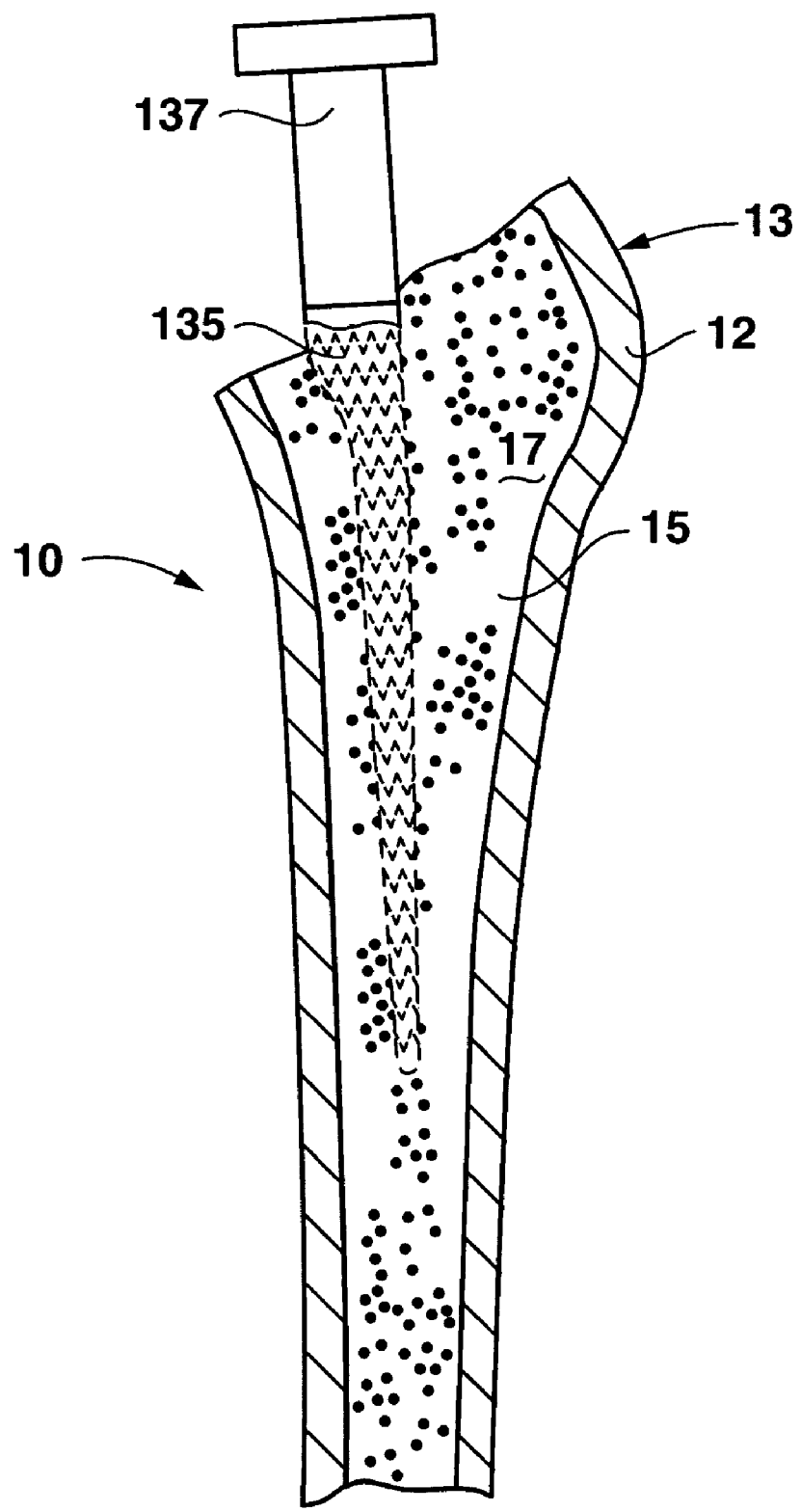
FIG. 3 is a depiction of a typical broaching of an intramedullary canal potentially applicable to the method of the invention.

After the intramedullary canal 15 has been accessed, in the method according to the invention, as shown in FIG. 3, it is preferred that a rough surfaced broach or awl 135, typically about 6-8 inches long and tapering from approximately 10-12 mm (proximal) to 5-6 mm (distal), which is removably mounted on the end of an impacting tool 137, is used to remove a small amount of cancellous bone 17 from the intramedullary canal 15 of the femur 10 to provide a starting space for impaction of the tamps 20.

While in most current primary total hip arthroplasties, the intramedullary canal is fully broached, using broaches of increasing size, down to the cortical bone 12 to provide a space for the placement of the femoral component of the hip prosthesis, this is where the current invention differs. For example, in my prior U.S. Pat. Nos. 5,910,172 and 6,589,285, only after the intramedullary canal has been fully broached are bone fragments dropped into the empty intramedullary canal and then tamped.

With the current invention, however, after the intramedullary canal 15 is accessed, only a small amount of broaching or awling will typically be done, typically using the smallest sized rough surfaced broach or awl 135 available. This is preferred to make impaction of the first tamp 20a easier. However, in certain cases, it may be possible to omit the broaching step altogether, depending upon the quantity and quality of the patient's cancellous bone 17.

As shown in FIG. 5A, the first tamp 20a may then be inserted into the intramedullary canal 15. The tamp 20a is then driven progressively further into the intramedullary canal 15 by applying successive driving forces (such as by a hammer, not shown) to a tamp handle 138. This progressive movement of the tamp 20a further into the intramedullary canal 15 continues until the doctor judges the tamp 20a to be fully and properly seated within the intramedullary canal 15 of the femur 10 (FIG. 5B). This can typically be achieved by the doctor matching a desired hash mark 150 on tamp handle 138 with the remaining portion of the greater trochanter 13. This is important to ensure proper leg length and offset are achieved.

At this position, the cancellous bone 17 has been pushed radially outward by the tamp 20a and is tightly packed against the tamp 20a and against the cortical bone 12 of the femur 10. If necessary, rod R may be inserted in bore 41 of tamp 20a to manually check for proper anteversion, varus, and valgus. Based upon the 20° angle bore 41 makes with respect to the transverse axis of tamp 20a, if rod R sticks straight out of the incision, the anteversion is correct. If not, the doctor may manipulate rod R until it does stick straight out of the incision or makes whatever alignment the doctor feels is required. Alternatively, bore 41 may be used as a reference point under fluoroscopy to check for varus, valgus, and anteversion. When the leg being operated on is properly positioned and viewed under fluoroscopy, the bore 41 will be seen in its full width (diameter), due to the already built in 20° angle it has with respect to tamp 20. Further alternatively, bore 41 may be positioned in tamp handle 138.

The tamp 20a is then withdrawn from the intramedullary canal 15. The cancellous bone 17 remains tightly packed against the cortical bone 12 of the femur 10 even after the tamp 20a is withdrawn from the femur 10 and forms a very accurately shaped, sized, and positioned cavity 29a in the cancellous bone 17 of intramedullary canal 15 having a shape of tamp 20a. In some instances, where the patient's cancellous bone 17 is very soft, it is possible for cavity 29a to not be completely surrounded by cancellous bone 17, i.e., small amounts of cortical bone 12 will be exposed to cavity 29a. These small amounts of cortical bone are insignificant in comparison to the prior art methods previously described. However, this aspect of the od is still within the scope of the invention.

As shown in FIGS. 6A, 6B, 6C, larger tamp 20b is now inserted into the cavity 29a formed by tamp 20a and the steps discussed in the last three (3) paragraphs are repeated to pack the cancellous bone 17 tightly against the cortical bone 12 of the femur 10 and the tamp 20b. Leg length, anteversion, varus, and valgus, may be re-checked, as previously described.

The tamp 20b is then withdrawn from the intramedullary canal 15. The cancellous bone 17 remains tightly packed against the cortical bone 12 of the femur 10 even after the tamp 20b is withdrawn from the femur 10 and forms another very accurately shaped, sized, and positioned cavity 29b in the cancellous bone 17 of intramedullary canal 15 having a shape of tamp 20b. However, the cavity 29b has increased in size from that of cavity 29a and the cancellous bone 17 has been even further packed in the radial direction.

Figure 8:
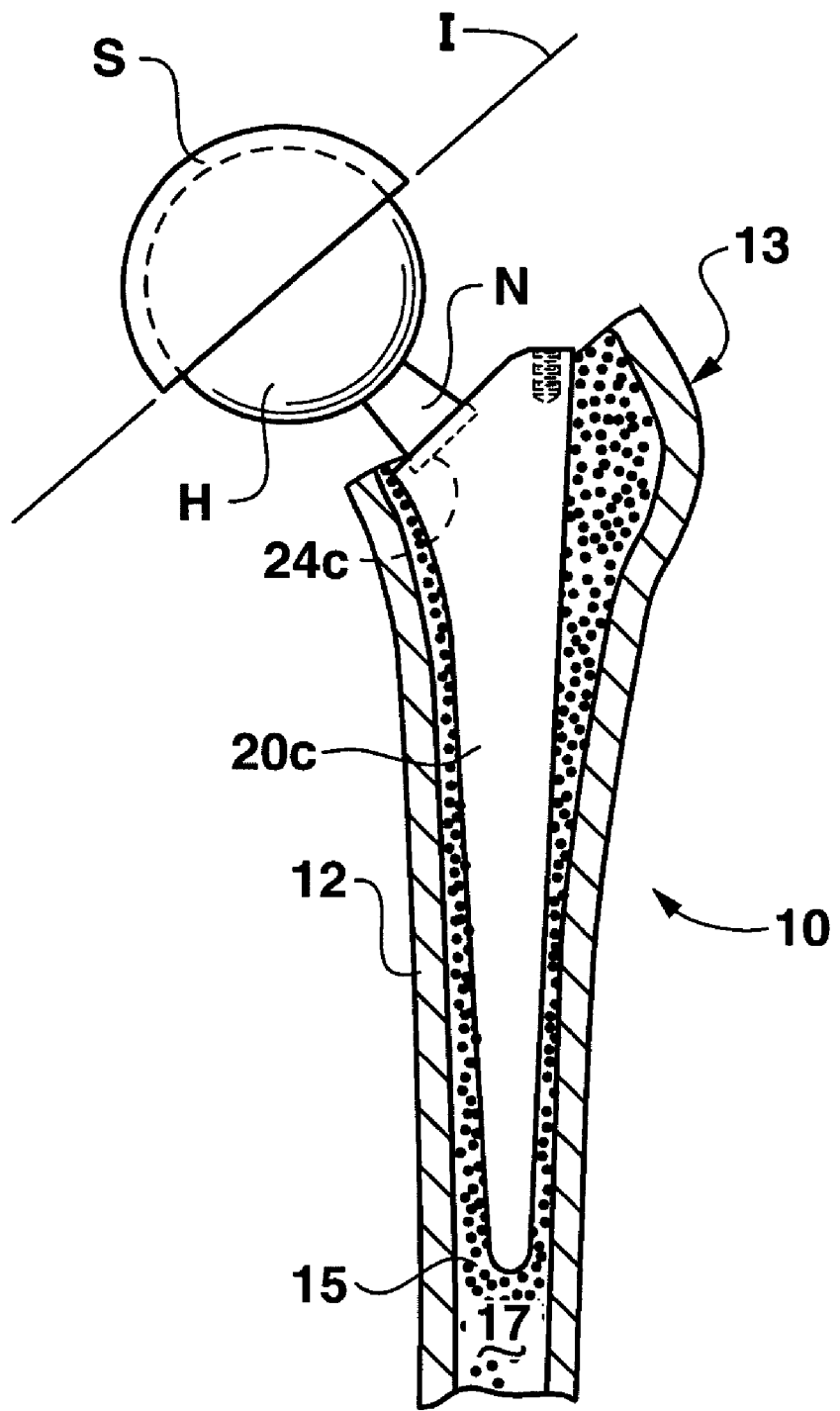
FIG. 8 depicts the use of the exemplary tamp according to the invention with a trial reduction.

As shown in FIGS. 7A, 7B, 7C, the final and largest tamp 20c is then inserted into the cavity 29b formed by tamp 20b and is driven into the intramedullary canal 15 as previously described until the doctor judges the tamp 20c to be fully and properly seated within the intramedullary canal 15 of the femur 10. As previously mentioned, final tamp 29c may comprise a "trial" which is a component sized and shaped to match the femoral component so that the doctor can determine sizings and clearances without risk to the final femoral implant. Furthermore, the doctor may remove tamp handle 138, while leaving tamp 20c within the intramedullary canal 15 to perform a trial reduction. To perform such a trial reduction, as shown in FIG. 8, a trial femoral neck N and head H may be positioned on the tamp 20c, via bore 24. Head H is then fitted within an acetabular shell S previously implanted within the patient's ilium 1. Leg length and range of motion can now be verified. This ability to perform trial reductions is not found in prior art one-piece tools, such as shown in U.S. Pat. No. 5,899,907.

After the optional trial reduction and the doctor re-checking for final leg length, varus, valgus, anteversion and positioning, the tamp 20c is then withdrawn from the intramedullary canal 15. What now results is a cavity 29c that closely if not precisely conforms to the shape and size of the prosthesis to be implanted and is extremely accurately shaped, sized, and positioned. This is due to the fact that, as previously mentioned, the final tamp in the series will preferably have a size and shape that is precisely the same as the prosthesis P to be implanted. Therefore, when prosthesis P is implanted, it will precisely match the position in which the trial reduction was carried out. This results in an extremely accurately positioned final prosthesis P and the doctor will not have to possibly remove the final prosthesis P and use a different sized prosthesis P, because the trial reduction does not match up with the actual reduction, resulting in wasted prostheses. Prior art trials after broaching are not nearly as accurate because they did not create a cavity that is as accurately shaped, sized, and positioned, as with the invention.

Figure 9:
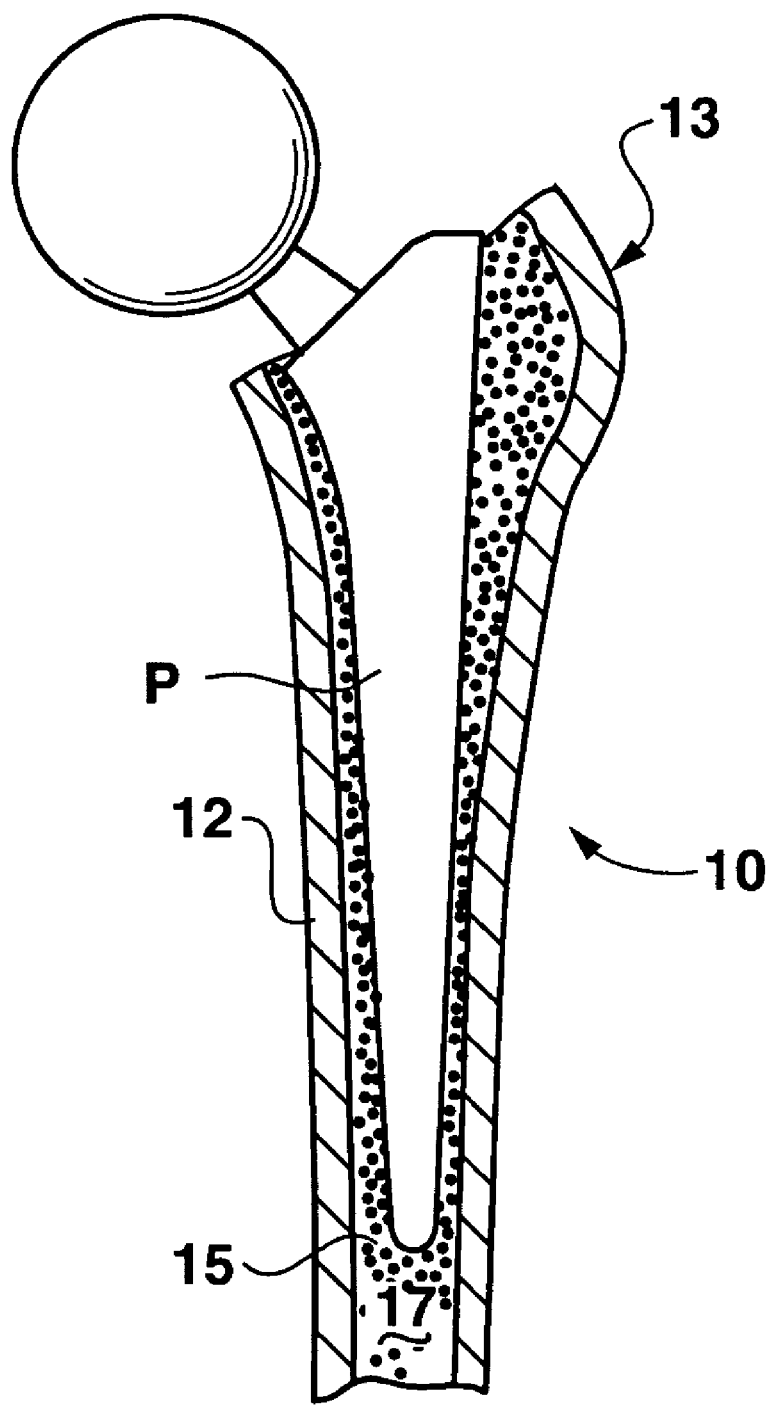
FIG. 9 depicts the femoral prosthesis implanted within the intramedullary canal of the femur according to the method of the invention.

As shown in FIG. 9, the prosthesis P is inserted into the final cavity 29c and is therefore completely surrounded by cancellous bone 17. The prosthesis P may be made from a suitable material such as: titanium, CoCr, or stainless steel. Furthermore, the body of the prosthesis may be polished, grit blasted, or porous. The stem portion of the prosthesis P has a shape corresponding to the shape of the body 21*c* of tamp 20*c*. In general, prosthesis P is smaller and less bulky than a prosthesis that would have been implanted in the same femur 10 according to prior art methods because there is now cancellous bone 17 at least partially filling intramedullary canal 15 and the prosthesis P is implanted in a cavity 29*c* in that cancellous bone 17. The intramedullary canal 15 is no longer completely emptied of its cancellous bone 17.

After the prosthesis P has been implanted in cavity 29*c*, over time, the cancellous bone 17 surrounding the prosthesis P will provide significant benefits.

First, in the event that revision surgery is later required by the patient, there is less risk of damage to the remaining femoral cortical bone because there will be no exposed cortical bone within the intramedullary canal after the primary implant is removed. This difference is depicted in FIGS. 10A and 10B. FIG. 10A depicts a cross section of a femur 200*a* after the primary hip stem, which was implanted according to conventional primary THA methods, has been extracted. As mentioned above, in the conventional implantation method, all cancellous bone is removed from the intramedullary canal 15 via broaching. Therefore, when the primary THA implant is removed, the inner walls 12' of cortical bone 12 are exposed to the intramedullary canal 15 and any metallic instrumentation inserted therein, which may fracture the cortical bone 12. Additionally, during the original primary broaching, it is possible that if the doctor broaches too deeply, cortical bone will also be undesirably removed. However, when the method of the invention is employed, cancellous bone 17 is left inside intramedullary canal 15 of femur 200*b*. As shown in FIG. 10B, the cancellous bone 17 that was tamped during the method according to the invention will form a boundary between any metallic instruments inserted into the intramedullary canal 15 and the cortical bone 12 of femur 200*b*.

Second, there is more bony support available, in the form of the cancellous bone 17, should revision become necessary.

Third, femoral bone remodels over time in the presence of an implant. In the presence of canal filling stems, as described above, where all the cancellous bone is removed, significant proximal femoral bone loss (stress shielding) is known to occur. In contrast, when, as previously described, less bulky, non-canal filling stems are used with the method of the invention it has been shown that the upper femoral bone can maintain its strength. This is particularly important as there are now implants and bearing surfaces available with the possibility of lasting 30 years or more. This permits the use of THA in younger patients.

Furthermore, an additional benefit to the method according to the invention is that autograft is used. This means there are no issues with respect to tissue matching and/or rejection. Additionally, the autograft is not harvested from another part of the patient's body, potentially causing complications, extended surgery times while the graft is harvested, or infections. The autograft actually remains in the intramedullary canal and is merely compacted in that same location.

Although this invention has been disclosed and illustrated with reference to particular exemplary embodiments, the principles involved are susceptible for use in numerous other embodiments which will be apparent to persons of ordinary skill in the art. The invention is, therefore, to be limited only as indicated by the scope of the appended claims.

That which is claimed:

1. A method for performing hip surgery, comprising the steps of:

providing a prosthesis to be implanted, accessing the intramedullary canal of a femur, said intramedullary canal containing native and existing cancellous bone; providing a first tamp, said tamp having a shape substantially similar to that of the prosthesis to be implanted; impacting said first tamp into said native and existing cancellous bone of said intramedullary canal; removing said first tamp, thereby forming a first cavity having a shape substantially similar to that of the prosthesis to be implanted in said cancellous bone of said intramedullary canal, and repeating the providing a first tamp, impacting and removing steps with a series of at least two progressively larger tamps, each said tamp having a shape substantially similar to that of the prosthesis, said series including a final tamp, said final tamp having a size substantially similar to that of the prosthesis to be implanted in said intramedullary canal; such that when said final tamp is removed a final cavity having a size and shape substantially similar to that of the prosthesis to be implanted is formed in said native and existing cancellous bone for receipt of said prosthesis, each said tamp having a bore for receipt of an adjustment rod, wherein each said tamp has a transverse axis and said bore is at an acute angle with respect to said transverse axis to thereby position the adjustment rod for use in verifying anteversion via the adjustment rod in the bore, said bore formed through a side of said tamp adjacent a proximal end of said tamp, using said bore for said adjustment rod for determining the position of said tamp by fluoroscopy, and implanting the prosthesis into said final cavity without using bone cement.

2. The method of claim 1, wherein said final cavity includes a wall of compressed and compacted cancellous bone that protects the cortical bone of said intramedullary canal.

3. The method of claim 1, wherein said step of providing further comprises providing tamps having smooth surfaces.

4. The method of claim 1, wherein said step of providing further comprises providing tamps, each said tamp having a trial neck bore therein, each said trial neck bore configured for receipt of a trial neck.

5. The method of claim 1, further comprising the step of using a tamp handle that is inline with the longitudinal axis of said tamp to insert said tamp.

\* \* \* \* \*